United States Patent [19]
Wright et al.

[11] Patent Number: 5,756,357
[45] Date of Patent: May 26, 1998

[54] METHOD FOR DETECTING HYDROCARBONS IN SOIL

[75] Inventors: Keith A. Wright; George A. Wheeldon, both of Placerville, Calif.; Theodore B. Lynn, Hamden, Conn.

[73] Assignee: Dexsil Corporation, Hamden, Conn.

[21] Appl. No.: 557,562

[22] Filed: Nov. 14, 1995

Related U.S. Application Data

[63] Continuation-in-part of Ser. No. 411,851, Mar. 28, 1995, abandoned, which is a continuation of Ser. No. 52,630, Apr. 27, 1993, abandoned.

[51] Int. Cl.$^6$ ........................... G01N 33/24; G01N 33/28
[52] U.S. Cl. ........................... 436/29; 436/25; 436/27; 436/28; 436/40; 436/60; 436/139; 422/68.1; 73/61.44; 73/863.12
[58] Field of Search ........................... 436/25, 27–31, 436/40, 60, 139, 20, 22, 23; 422/61, 68.1, 99, 101; 73/61.43, 61.44, 153, 155, 863.12, 866

[56] References Cited

U.S. PATENT DOCUMENTS

| | | | |
|---|---|---|---|
| 2,311,151 | 2/1943 | Campbell | 250/252.1 |
| 2,312,271 | 2/1943 | Smith | 436/31 |
| 2,431,487 | 11/1947 | Larsen | 250/301 |
| 2,500,213 | 3/1950 | Stevens | 250/255 |
| 2,712,986 | 7/1955 | Huckabay | 436/31 |
| 3,524,436 | 8/1970 | Schmidt | 406/134 |
| 3,746,511 | 7/1973 | Stookey et al. | 23/231 |
| 4,046,668 | 9/1977 | Farcasiu et al. | 208/11 LE |
| 4,343,897 | 8/1982 | Neumann et al. | 435/19 |
| 4,485,071 | 11/1984 | Larter | 422/78 |
| 4,944,921 | 7/1990 | Colby et al. | 422/70 |
| 4,980,295 | 12/1990 | Udy | 436/21 |
| 4,992,379 | 2/1991 | Hanby | 436/29 |
| 5,155,546 | 10/1992 | Balsam et al. | 356/300 |
| 5,181,428 | 1/1993 | Chriswell | 73/863.12 |
| 5,288,643 | 2/1994 | Sadhir et al. | 436/60 |
| 5,306,643 | 4/1994 | Sadhir et al. | 436/140 |

OTHER PUBLICATIONS

Zhang et al., Determination of a small amount of crude oil in soil using tetrahydrofuran–turbidimetric method, Huanjing kexye Journal, Abstract, 9(4), 57–8, 52, 1988.

Rapid & Convenient Laboratory Method for Extraction & Subsequent Spectrophotometric Determination of Bitumen Content of Bituminous Sands, M.S. Patel, Analytical Chemistry, vol. 46, No. 6, May 1974.

*Primary Examiner*—Harold Y. Pyon
*Attorney, Agent, or Firm*—Law Office of Victor E. Libert; Frederick A. Spaeth

[57] ABSTRACT

The presence of hydrocarbons in soil is detected by immersing a soil sample in a water-miscible solvent capable of dissolving the hydrocarbons to extract hydrocarbons from the soil into the solvent. An aqueous developer is mixed into the solvent to produce a test mixture. The turbidity of the test mixture is observed to determine the presence of hydrocarbons in the soil. The aqueous developer may contain at least 0.5% salt, e.g., at least 1%, preferably 5% salt, and an emulsifier. Turbidity may be measured quantitatively by measuring light scattered at 90° to a test light beam or by visual comparison to a reference scale.

11 Claims, 1 Drawing Sheet

COMPARATIVE EXAMPLE

METHOD FOR DETECTING HYDROCARBONS IN SOIL

This application is a continuation-in-part of U.S. patent application Ser. No. 08/411,851, filed Mar. 28, 1995, now abandoned, which was a continuation of U.S. patent application Ser. No. 08/052,630, filed Apr. 27, 1993, now abandoned.

BACKGROUND OF THE INVENTION

1. Field of the Invention

This invention relates to a method for detecting hydrocarbons in soil, and in particular to a method comprising extracting the hydrocarbons from the soil using a water miscible solvent.

It is now well accepted that corporations and individuals have a legal duty to protect the environment, including soil, against contamination by the inadvertent release of oil or other hydrocarbons, and that remedial measures must be taken should such accidents occur. Various tests have been developed to enable investigators to detect the presence of hydrocarbons in soil to help identify sites of releases from leaking storage tanks and other sources of contamination. Other tests for hydrocarbons in soil have been developed for the mining industry to help locate drilling sites for petroleum recovery.

2. Related Art

U.S. Pat. No. 2,431,487 to Larsen, dated Nov. 25, 1947, discloses a method for detecting oil in drilling mud. The method involves mixing mud with a solvent for the oil which is miscible with water, to extract the oil into the solvent. A water-miscible solvent is used so that the solvent can penetrate the aqueous phase within which the oil resides in the mud, so that the solvent has immediate contact with the oil and a single phase within which the oil resides is created (see column 3, lines 24 through 34). A broad range of solvents is identified for use in the process, including ketones, alcohols, glycols and the like (see column 2, lines 7 through 16). Before adding the solvent, the mud may be diluted with water. Alternatively, the solvent may be mixed with water before it is added to the mud (see column 5, lines 34 through 38). After extracting the oil, the solvent is examined by exposure to ultraviolet light, and if the solvent fluoresces, oil is said to be present therein. Other analytical methods may be used to detect the oil, e.g., infrared adsorption, spectrophotometric analysis and the like (see column 3, line 72 through column 4, line 19). To better observe fluorescence, Larsen teaches a preference for a clear solution (see column 3, lines 50 through 54).

Mahendra Patel, in an article entitled *Rapid and Convenient Laboratory Method for the Extraction and Subsequent Spectrophotometric Determination of Bitumen Content in Bituminous Sands*, published in 46 Analytical Chem., No. 6, May 1974, discloses a method for determining the quantity of bitumen in sand. A sample of the sand is washed with an extraction solvent (toluene) to extract the bitumen from the sand. The solvent is subjected to photometric analysis, and the measured absorbance is compared against a calibration curve produced by analyzing a known test solution.

SUMMARY OF THE INVENTION

The present invention provides a method for detecting hydrocarbons in soil. According to this method, a soil sample is immersed in a water-miscible solvent capable of dissolving hydrocarbons to extract hydrocarbons from the soil into the solvent. The solvent is mixed with an aqueous developer to produce a test mixture comprising the solvent, the aqueous developer and the hydrocarbons extracted into the solvent. Then the turbidity of the test mixture is observed to determine the presence of hydrocarbons in the soil.

According to another aspect of the invention, the aqueous developer may be mixed with the solvent in an amount that yields a test mixture comprising from about 30 to 70 weight percent solvent, preferably 30 to 40 weight percent solvent, and the solvent preferably comprises alcohol.

According to still another aspect of the invention, the method may comprise illuminating the test solution with a test beam from a light source and observing the intensity of light scattered from the source. Observing the intensity of light scattered from the source may comprise observing scattered light from a point not in the path of the test beam illuminating the test mixture, for example, measuring the intensity of light scattered from the test mixture at an angle of about 90° relative to the test beam.

According to still another aspect of the invention, the method may comprise comparing the turbidity of the test mixture to a reference scale to assess the quantity of hydrocarbons in the soil.

Yet another aspect of the invention provides that the aqueous developer may comprise at least about 0.5% salt, e.g., at least about 1% salt, preferably, about 5% salt. The aqueous developer may also comprise an emulsifier, which may be present in an amount of about 1000 ppm of the aqueous developer.

DETAILED DESCRIPTION OF THE INVENTION AND PREFERRED EMBODIMENTS THEREOF

Figure 1:
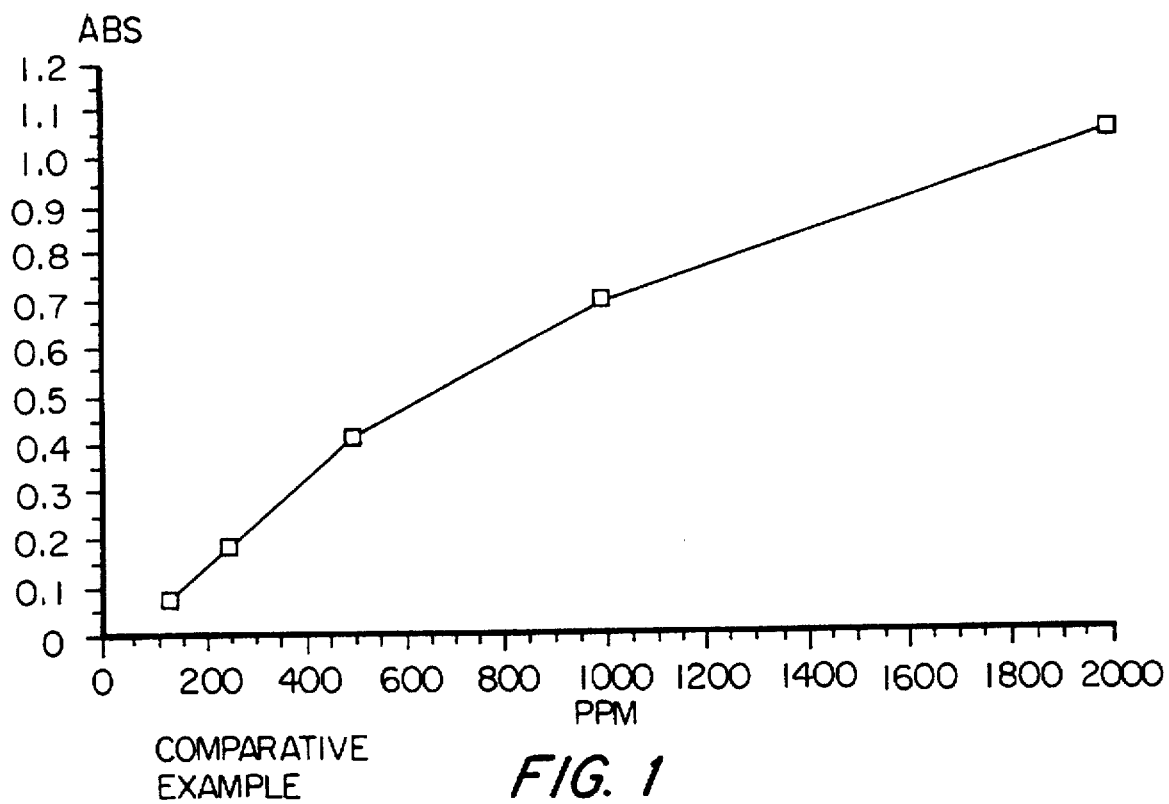
FIG. 1 is a plot of spectrographic absorbance of a test mixture on the vertical axis vs. hydrocarbon concentration of the soil samples from which the test mixture hydrocarbons were derived on the horizontal axis, wherein the emitted light is measured at a point 180° in line with the test beam.

The present invention relates to a test for the detection of hydrocarbons in soil. Contrary to the teachings of the prior art, the method of the present invention involves extracting the hydrocarbons from the soil sample using a solvent that is miscible with water and which, when water is added, forms a turbid mixture when hydrocarbons are present therein, due to the formation of an emulsion of the hydrocarbons in the test mixture.

The claimed method provides distinct advantages over prior art methods for the detection of hydrocarbons in soil. First, by creating a solvent-water test mixture that becomes turbid in the presence of the hydrocarbons, the claimed method can be practiced without the need for a spectrophotometer or other light-intensity measuring devices or special light sources required in the prior art. Generally, the eye is well attuned to the detection of turbidity so the invention provides a very sensitive yes/no test for the presence of hydrocarbons and, with the use of a reference turbidity scale, allows a user to make an accurate quantitative assessment of the hydrocarbon content of the sample based on the visually discerned degree of turbidity of the test mixture.

Second, conventional photometric devices are more sensitive to turbidity than to fluorescence, so the present invention permits the user to detect hydrocarbons in soil at levels lower than the method taught by Larson in U.S. Pat. No. 2,431,487. Turbidity will indicate, at a statistical confidence level of 99%, the presence of as little as 13 ppm diesel fuel or 18.6 ppm used motor oil in a solvent comprising 75% methanol and 25% ethanol disposed in a test mixture comprising 70% water by weight. The water in such a test should contain 5% salt and 1000 parts per million RW-100™ emulsifier.

Solvents that may be employed in the practice of the present invention include ketones such as acetone, methylethylketone, and diethylketone; diethylene glycol, ethylene glycol mono-ethyl-ether; ethylene glycol mono-butyl-ether; polypropylene glycol; triethylene glycol; dimethyl-sulfoxide; acetonitrile; diethylene glycol dimethyl ether; a mixture of about 10–90% acetone with a $C_1$ to $C_6$ alcohol; glacial acetic acid; a mixture of about 10–90% glacial acetic acid with a $C_1$ to $C_6$ alcohol; a mixture of methyl-ethylketone with a $C_1$ to $C_6$ alcohol; and $C_1$ to $C_6$ alcohols and mixtures thereof, methanol being generally preferred. In testing for gasoline, ethanol has been found to be an unsuitable solvent, but methanol works well. In testing for crude oil, isopropanol is preferred. Solvents which are not suitable by themselves for use with the present invention include acetone, ethylacetate ester, petroleum ether, hexane, phenol, methylethylketone, toluene and benzene.

The claimed method may be practiced with a wide range of water-based solutions, in addition to pure water, which are referred to herein collectively as "aqueous developers" since they appear to elicit turbidity in the solvent when hydrocarbons are dissolved therein. Thus, the invention may be practiced using colorless water or whatever clear, lightly tinted water happens to be available in the field, e.g. where no other aqueous developer is available, a clear soft drink such as tonic water or ginger ale. The mixture of the aqueous developer and the solvent is sometimes referred to herein and in the claims as the "test mixture".

Generally, the invention is practiced by depositing a soil sample of known weight into a volume of the solvent, and mixing the soil therein to allow the solvent to extract the hydrocarbons, if any, that are present therein. The aqueous developer is then added to the solvent in generally equal volume thereto, to create the test mixture. The water-to-solvent ratio in the test mixture may be from about 3:1 to 1:3 by volume, i.e., the solvent may comprise from about 25% to 75% of the test mixture, by volume. The turbidity of the test mixture indicates the presence of hydrocarbons, as described below.

The turbidity of the test mixture may be observed in any convenient manner, e.g., by visually observing the test solution in ambient light. However, in a particular embodiment of the invention, the turbidity of the test mixture is observed by directing a light beam of known intensity into the test mixture and observing the intensity of scattered light emitted therefrom. In a particular embodiment, light of a wavelength of 530 nm is employed. Preferably, the scattered light is measured from a point where light would not be received from the test beam were the beam to pass through the test mixture. Thus, this aspect of the invention provides a measurement technique that differs from the techniques used for spectrographic analysis, in which a test beam is aimed directly at a light-intensity sensor in a path that passes through the solution. A device well-suited to measure the intensity of scattered light is known as a two-channel 90° scattered light meter. As will be shown below, measuring scattered light at an angle of 90° to the test beam can allow the plotting of an intensity-hydrocarbon content curve from fewer samples than direct, in-line measurement at 180°.

Since the present invention relies on the development of turbidity in a test mixture to indicate the presence of an analyte, it is advantageous to filter the test mixture to remove particulates that would falsely enhance the turbidity of the mixture. A suitable filter system for this purpose is a sintered polyethylene filter having a 20 micron pore size followed by a 0.2 micron pore size filter. The analyte may be filtered using a syringe having filters positioned in the syringe barrel. Disk-type filters may be used, but it is preferred to use filters having greater surface areas than can be attained with a disk-shaped filter. For example, the 20 micron filter may have a conical configuration or may be configured to comprise a plurality of conical protuberances, to afford increased surface area. The Applicants have found that by adding salt, e.g., NaCl, $CaCl_2$, $Na_2SO_4$, to the aqueous developer, the emulsion caused by the presence of lighter hydrocarbons in the test mixture is enhanced. It is believed that the addition of salt to the aqueous developer reduces the solubility of the hydrocarbon contaminant in the test mixture. At least about 0.5% by weight salt should be included in the aqueous developer to enhance the sensitivity of the test mixture. However, it is preferred to use more than this quantity of salt since soil samples can contain varying quantities of background salt that may be inherent in that type of soil or which may have been deposited therein as road salt, sea spray, etc. Whatever the source of background salt, variations in salt levels in soil samples can cause discernible variations in the turbidity sensitivity of the test mixture. To ameliorate such variations, it is preferred to use at least 1% salt, more typically 5% salt, in the aqueous developer.

The presence of significant quantities of salt in the test mixture can render the emulsion unstable so that, after a short time, the hydrocarbon phase separates from the miscible solvent-aqueous developer phase. To prevent such separation, the Applicants have found that addition of about 1000 ppm of an emulsifier will be effective to preserve the turbidity of the test mixture.

In a typical embodiment, the aqueous developer may comprise 5% sodium chloride and 1000 ppm of an alkylamine-ethoxylate emulsifying agent available from the Union Carbide Corporation under the trade designation Triton RW-100™. This developer may be used in combination with a solvent comprising 75% methanol and 25% ethanol by weight. Other emulsifying agents that have been found to be effective include trisodium phosphate, sodium dodecylsulfate, polyoxyethylenesorbitan, and alkylaryl polyether alcohols.

To obtain a quantitative determination for the presence of hydrocarbons in the soil samples, the turbidity of the test mixture is compared against a reference turbidity scale, e.g., a reference set of turbid mixtures derived from soil samples of known hydrocarbon content. A "laboratory" reference set can be prepared from a sand or soil specimen that is known to be clean, i.e., free of pollutant hydrocarbons. It is preferred that the reference specimen be of the same type as that at the test site; for this purpose, reference may be made to the soil survey published by the United States Department of Agriculture in which soil types for locations across the culture are classified. A clean test sample is taken from the specimen and is set aside. A clean portion of the specimen is also set aside; the remaining portion is innoculated with a known quantity of hydrocarbons such as gasoline or diesel fuel and the specimen and hydrocarbons are mixed together thoroughly so that the specimen portion is uniformly contaminated with the hydrocarbons. Preferably, the hydrocarbon employed is of the same type as that suspected of being present at the test site. A sample is taken from the contaminated portion, and an additional, known quantity of the clean portion of the specimen is mixed into the remaining contaminated portion in an amount that reduces the relative pollutant content of the contaminated portion by a convenient amount, e.g., 100 parts per million (ppm). A sample is taken and another quantity of clean specimen is mixed into the remaining contaminated specimen to further dilute the hydrocarbon content. This procedure is repeated to yield a series of test samples having a steadily decreasing hydrocarbon content. Alternatively, the initial innoculation may involve a minimal quantity of hydrocarbons, and after the first sample is taken, additional hydrocarbon may be added to the remaining specimen in known amounts, to produce a series of samples of increasing hydrocarbon content. In either case, each of the samples is subjected to a test procedure as described herein. The test mixture derived from the clean test sample will be clear and will represent zero ppm hydrocarbons. The other test mixtures will exhibit varying degrees of turbidity. The turbid mixtures can be retained for as long as the turbidity remains stable and can be used as a reference scale for comparison against tested field samples. Optionally, the turbidities of the reference samples may be measured using a suitable instrument to produce one or both of a turbidity-versus-hydrocarbon content graph or a database against which the turbidity of field samples can be compared.

If a laboratory reference set is not available, or if it is necessary or desired to compare the hydrocarbon content of a test site against that of a nearby soil, a so-called "site-specific" reference set may be produced. The site-specific reference set may be produced by taking a specimen of "clean" soil from a point near the test site. The "clean" soil will be deemed to contain an acceptable level of hydrocarbons, e.g., "background" or naturally-occurring hydrocarbons, and will therefore provide a base-line against which a sample from the test site will be measured. Background hydrocarbons can be present in soil due to the presence of pine needles, tree sap, and other environmental sources. The site-specific reference set can be produced in the same way a laboratory reference set is produced. If a laboratory reference set is available, the clean site specimen may be tested and compared against the zero ppm laboratory reference set sample. If the site-specific baseline sample yields a test mixture that is as clear as that of the zero ppm laboratory reference set sample, it indicates that the site has virtually no background hydrocarbons and that the laboratory reference set may be used as a direct indicator of the hydrocarbon content of the site in question. On the other hand, if the site-specific baseline sample is turbid due to the presence of background hydrocarbons, the level of background hydrocarbons can be determined by comparison to the laboratory reference set. A differential hydrocarbon level measurement for the test site can be made by comparing the test site test mixture to the laboratory reference set and making the appropriate adjustment indicated by the level of background hydrocarbons at the test site.

The method of the claimed invention will be better understood with reference to the following examples:

EXAMPLE 1

A typical test procedure in accordance with one embodiment of the invention is as follows.

A clean, dry, ten milliliter or larger test tube is placed on a test tube support. A funnel is situated with its cannula in the test tube. A cotton ball is placed in the apex of the funnel and a paper filter is inserted into the funnel. Preferably, an air space is provided between the rim of the test tube and the side of the funnel.

A soil sample weighing five grams is placed in a vial. Five milliliters of a solvent is added to the vial which is then shaken to extract hydrocarbons present in the soil into the solvent. The contents of the vial are poured into the funnel so that the liquid passes through the filter media, i.e., through the paper filter and cotton ball, and into the test tube. Then, sufficient deionized water is added to provide a total solvent-water test mixture volume of ten milliliters in the test tube. The presence of hydrocarbons in the test mixture will be evident by the turbidity of the test mixture.

EXAMPLE 2

A one-pound specimen of homogeneous soil was collected from a test site. A sample of this specimen, designated Sample A, was tested using methanol as the solvent and water as the aqueous developer. The test mixture was non-turbid, indicating an absence of hydrocarbons in the soil.

Five test samples weighing 50 grams each were taken from Sample A and were labeled B, C, D, E and F. Sample B was innoculated with one drop (approximately 0.05 milliliters) of a commercial automotive product known as STP™ fuel injector and carburetor cleaner. Sample C was innoculated with one drop of petroleum distillates. Sample D was innoculated with one drop of mineral spirits. Sample E was innoculated with one drop of naphthol, and Sample F was innoculated with one drop of chlorinated hydrocarbons. A 5 gram sub-sample of each of Samples B–F was tested in the same way as Sample A, and in each case, the test mixture became turbid.

EXAMPLE 3

A first soil specimen, designated S1, was taken from a location near a test site suspected of being contaminated with diesel fuel. Specimen S1 was believed to represent an uncontaminated sample of soil, i.e., to contain only background hydrocarbons, if any. A sample of specimen S1 was tested and the resulting test mixture was found to be clear, indicating the absence of hydrocarbons. A second, uncontaminated specimen designated S2 was taken from near the test site, and a site-specific reference set was produced using diesel fuel as the contaminant. Then, a test sample was taken from the test site. The test sample was tested and the resulting test mixture was turbid. By comparison to the site-specific reference set, it was determined that the test sample in question contained 500 ppm diesel fuel.

EXAMPLE 4

A laboratory soil specimen was prepared using four parts each of clays from two different locations and two parts sand, each sieved to <850 micron particle sizes. The composite was divided into several portions. The portions were innoculated with crude oil by dissolving the oil in hexane and mixing the hexane into a specimen portion. The hexane was allowed to evaporate until the specimen weight was stable, leaving a hydrocarbon-innoculated specimen portion. Samples were taken from portions innoculated with 1000 ppm crude oil, 500 ppm crude oil and 200 ppm crude oil as generally described above. A 10 gram sample was immersed in 10 grams of a solvent comprising 75% methanol and 25% ethanol. After the hydrocarbon contaminants were extracted into the solvent, the solvent was filtered and 4 grams of water comprising 5% NaCl and 1000 ppm of Triton X-100™ emulsifier were added to 2.2 grams of the solvent to create a test mixture.

The turbidity of each test mixture was tested in two ways. First, by measuring the degree of transmission of a test beam of light from a point 180° in line with the test beam. The results were plotted with absorbance on the vertical axis and hydrocarbon concentration on the horizontal axis, and the results are shown in FIG. 1.

Figure 2:
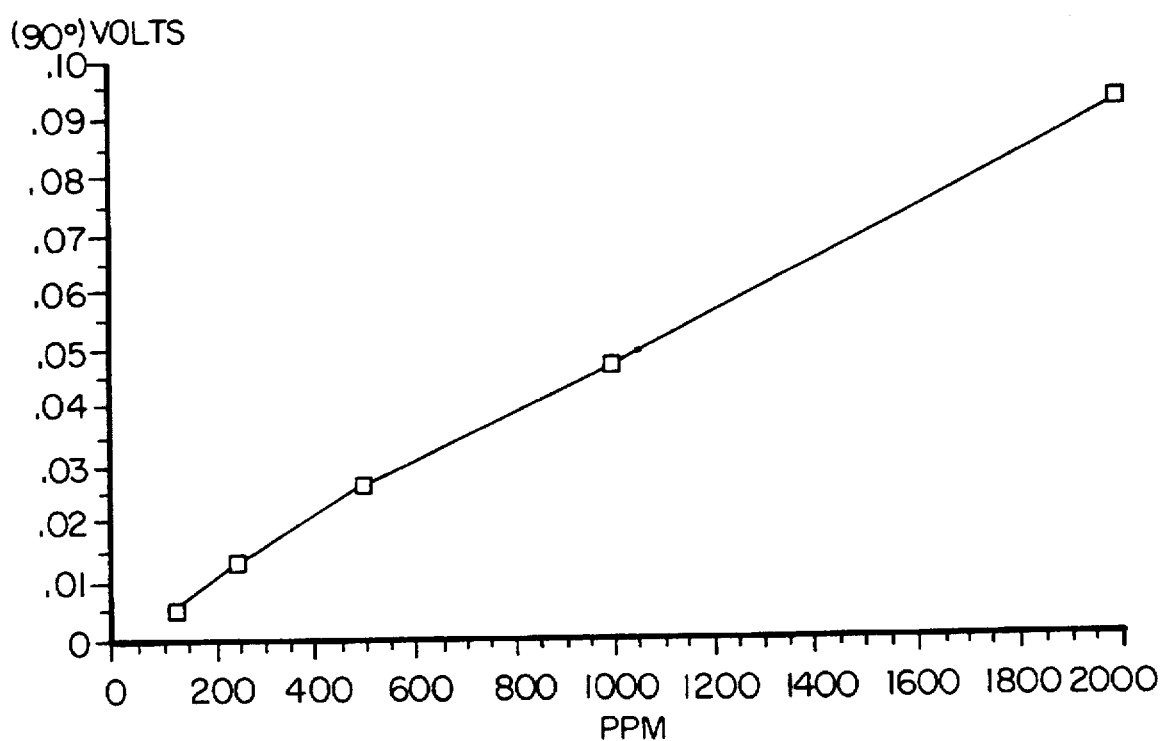
FIG. 2 is a plot of turbidity, measured as the intensity of light (in photocell volts) on the vertical axis measured at 90° relative to a test beam vs. hydrocarbon content of soil samples from which the test mixtures were derived on the horizontal axis.

The turbidity of each test mixture was also tested by measuring scattered light emanating from the test tube at an angle of 90° from the test beam. This assured that the reading did not take into account any portion of the test beam that may be transmitted through the solution to skew the results of measurements taken at 180°. The results of measurement at 90° are shown in FIG. 2 in which the vertical axis indicates intensity and the horizontal axis again indicates hydrocarbon concentration. It is clear by comparing FIGS. 1 and 2 that measurement from 90° gives a calibration curve that is more linear than that obtained by measuring absorbance at 180°. As a result, fewer reference samples need be prepared to create an accurate calibration curve using measurements at 90° than are required to accurately plot the curve for measurements at 180°. Thus, this aspect of the invention provides a distinct advantage over the prior art.

EXAMPLE 5

To determine how the sensitivity of the method, in accordance with the present invention, varies with the solvent-to-aqueous developer proportions, two solvents were innoculated with known quantities of diesel fuel as a contaminant, and portions of the solvent were mixed in varying proportions with an aqueous developer comprising 5% NaCl and 1000 ppm of Triton X-100™ emulsifier. The resulting test mixtures exhibited varying degrees of turbidity, which were measured using an absorbance photometer. The results are set forth below in TABLE I. The solvent in Sample A was methanol that contained 250 ppm diesel fuel by weight; the solvent in Sample B contained equal weight proportions of ethanol and methanol and contained 250 ppm diesel fuel; the solvent of Sample C was methanol that contained 50 ppm diesel fuel and the solvent of Sample D comprised equal portions of methanol and ethanol with 50 ppm diesel fuel therein.

TABLE I

ABSORBANCE READINGS

| Sample | Weight % H$_2$O Test Mixture | | | | |
|---|---|---|---|---|---|
| | 20 | 39 | 56 | 72 | 86 |
| A | 0 | 0.1 | 0.225 | 0.225 | 0.02 |
| B | — | — | 0.125 | 0.175 | 0.04 |
| C | 0 | 0 | 0.012 | 0.027 | 0 |
| D | 0 | 0 | 0 | 0.012 | 0.012 |

The data of TABLE I show that in general, when water constitutes about 60% to 70% of the test mixture, the test gives the strongest indication of the presence of hydrocarbons at a given contamination level. Thus, the optimum solvent content is from about 30% to 40% of the test mixture for alcohol solvents.

While the invention has been described in detail with reference to a particular embodiment thereof, it will be apparent that upon a reading and understanding of the foregoing, numerous variations to the described embodiment will occur to those skilled in the art and it is intended to include such variations within the scope of the appended claims.

What is claimed is:

1. A method for detection of hydrocarbons in soil, comprising:

immersing a soil sample in a water-miscible solvent comprising alcohol, the solvent being capable of dissolving hydrocarbons, to extract hydrocarbons from the soil into the solvent;

filtering the solvent after extracting hydrocarbons from the sample;

mixing the solvent with an aqueous developer that comprises at least about 0.5% salt to produce a test mixture comprising the solvent, the hydrocarbons extracted into the solvent and the aqueous developer, the test mixture comprising from about 30% to 40% solvent by weight; and observing the turbidity of the test mixture to determine the presence of hydrocarbons in soil.

2. The method of claim 1 comprising mixing the solvent with the aqueous developer in an amount of from about 30% to 70% solvent by weight of the test mixture.

3. The method of claim 1 wherein the solvent comprises methanol.

4. The method of claim 1 further comprising comparing the turbidity of the test solution to a reference scale to assess the quantity of hydrocarbons in the soil.

5. The method of claim 1 wherein the aqueous developer comprises at least about 1% salt.

6. The method of claim 5 wherein the aqueous developer comprises about 5% salt.

7. The method of claim 1 wherein the aqueous developer further comprises an emulsifier.

8. The method of claim 7 wherein the emulsifier comprises about 1000 ppm of the aqueous developer by weight.

9. The method of claim 1 wherein observing the turbidity of the test mixture comprises illuminating the test solution with a test beam from a light source and observing the intensity of light scattered from the source.

10. The method of claim 9 wherein observing the intensity of light scattered from the source comprises observing scattered light from a point not in the path of the test beam illuminating the test mixture.

11. The method of claim 10 wherein observing the intensity of scattered light comprises measuring the intensity of light scattered from the test mixture at an angle of about 90° relative to the test beam.

* * * * *

UNITED STATES PATENT AND TRADEMARK OFFICE
CERTIFICATE OF CORRECTION

PATENT NO : 5,756,357
DATED : May 26, 1998
INVENTOR(S) : Keith A. Wright et al

It is certified that error appears in the above-identified patent and that said Letters Patent is hereby corrected as shown below:

On title page, under the heading "References Cited U.S. PATENT DOCUMENTS", replace "3,524,436" with --3,524,346--.

In column 1, lines 15-16, replace "water miscible" with --water-miscible--.

In column 3, line 6, replace "Larson" with --Larsen--;

line 12, insert "Triton" before "RW-100™";

line 37, insert a comma after "e.g.".

Signed and Sealed this

Seventh Day of September, 1999

Attest:

Q. TODD DICKINSON

Attesting Officer

Acting Commissioner of Patents and Trademarks